US010384051B2

(12) United States Patent
Pelssers et al.

(10) Patent No.: US 10,384,051 B2
(45) Date of Patent: Aug. 20, 2019

(54) DEVICE FOR INACTIVATING BACTERIA ON THE SURFACE OF THE STRATUM CORNEUM LAYER OF SKIN

(71) Applicant: KONINKLIJKE PHILIPS N.V., Eindhoven (NL)

(72) Inventors: Eduard Gerard Marie Pelssers, Eindhoven (NL); Mark Thomas Johnson, Eindhoven (NL); Johannes Hendrikus Maria Spruit, Eindhoven (NL); David Halter, Eindhoven (NL); Roland Cornelis Martinus Vulders, Eindhoven (NL); Robby Petrus Cornelis Van Dreumel, Eindhoven (NL); Marco Baragona, Eindhoven (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 0 days.

(21) Appl. No.: 15/306,850

(22) PCT Filed: Apr. 29, 2015

(86) PCT No.: PCT/EP2015/059373
§ 371 (c)(1),
(2) Date: Oct. 26, 2016

(87) PCT Pub. No.: WO2015/165986
PCT Pub. Date: Nov. 5, 2015

(65) Prior Publication Data
US 2017/0043154 A1 Feb. 16, 2017

(30) Foreign Application Priority Data

May 2, 2014 (EP) .................................. 14166869

(51) Int. Cl.
*A61N 1/30* (2006.01)
*A61N 1/04* (2006.01)
(Continued)

(52) U.S. Cl.
CPC .......... *A61N 1/0408* (2013.01); *A61L 2/0011* (2013.01); *A61L 2/03* (2013.01);
(Continued)

(58) Field of Classification Search
None
See application file for complete search history.

(56) References Cited

U.S. PATENT DOCUMENTS 5,019,034 A * 5/1991 Weaver ............. A61B 5/14514
604/20
5,439,440 A 8/1995 Hofmann
(Continued)

FOREIGN PATENT DOCUMENTS

RU 2477155 C2 3/2013
WO 2013066427 A1 5/2013

*Primary Examiner* — Kennedy Schaetzle

(57) ABSTRACT

The present application relates to a device for the electroporation of bacterial cells in or on a surface of the Stratum corneum layer of a person's skin. It comprises electrodes positionable in the vicinity of said surface; a generator to supply a voltage to the electrodes to generate an electrical field having a strength in the order of 25 to 35 KV/cm at said surface of the Stratum corneum layer to inactivate bacterial cells in or on said surface. The electrodes are configured so that the strength of the electrical field reduces as a function of the depth of penetration into the skin from 25 to 35 KV/cm at said surface to 3 KV/cm or less at a depth of penetration that does not exceed 15 microns. The electrical field generated by the device will have sufficient strength to inactivate bacteria cells present on the stratum corneum while at the same time this electrical field is not strong enough to appreciable effect living skin cells in the epider- (Continued)

mis below the stratum corneum or at the interface between the stratum corneum and the epidermis.

15 Claims, 8 Drawing Sheets

(51) Int. Cl.
  *A61N 1/32* (2006.01)
  *A61L 2/00* (2006.01)
  *A61L 2/03* (2006.01)
(52) U.S. Cl.
  CPC ............. *A61N 1/0412* (2013.01); *A61N 1/30* (2013.01); *A61N 1/325* (2013.01); *A61N 1/327* (2013.01)

(56) References Cited

U.S. PATENT DOCUMENTS

| | | | |
|---|---|---|---|
| 5,702,359 A | 12/1997 | Hofmann | |
| 5,968,006 A | 10/1999 | Hofmann | |
| 6,302,874 B1* | 10/2001 | Zhang | A61N 1/0424 604/501 |
| 6,711,435 B2* | 3/2004 | Avrahami | A61N 1/30 604/20 |
| 7,133,717 B2 | 11/2006 | Coston | |
| 8,705,223 B2* | 4/2014 | Villemejane | A61N 1/0412 249/83 |
| 2004/0230227 A1 | 11/2004 | Avrahami | |
| 2004/0267189 A1 | 12/2004 | Mavor | |
| 2006/0036209 A1* | 2/2006 | Subramony | A61M 37/0015 604/20 |
| 2007/0060862 A1 | 3/2007 | Sun | |
| 2008/0063866 A1* | 3/2008 | Allen | A61B 5/685 428/389 |
| 2009/0048651 A1 | 2/2009 | Andino | |
| 2013/0260435 A1 | 10/2013 | Pakhomova | |
| 2014/0378964 A1* | 12/2014 | Pearson | A61B 18/1477 606/41 |

* cited by examiner

DEVICE FOR INACTIVATING BACTERIA ON THE SURFACE OF THE STRATUM CORNEUM LAYER OF SKIN

This application is the U.S. National Phase application under 35 U.S.C. § 371 of International Application No. PCT/EP2015/059373, filed on Apr. 29, 2015, which claims the benefit of International Application No. 14166869.9 filed on May 2, 2014. These applications are hereby incorporated by reference herein.

FIELD OF THE INVENTION

The present invention relates to a device for inactivating bacteria. A method of manufacturing such a device is also disclosed.

BACKGROUND OF THE INVENTION

Human skin has two broad tissue types, the epidermis and the dermis. The epidermis is a continually keratinizing stratified epithelium. The outermost layer of skin is the stratum corneum and functions as the primary barrier. The stratum corneum is the outermost layer of the epidermidis and varies in thickness as function of the skin location. For example in the hand palm this layer can reach a thickness of 300 micron while the thickness in the armpit is approximately 5 to 15 micron. The stratum corneum is 15-30 cell thick layer of non-viable corneocytes.

The electroporation of cells is a non-thermal technique in which electrical fields are used to create nano-scale defects in a cell's membrane, which may cause cell inactivity or death. Electroporation involves the application of brief electrical pulses that result in the creation of aqueous pathways within the lipid bi-layer membranes of biological cells. Electroporation depends on the local transmembrane voltage at each point on the cell membrane. It is generally accepted that for a given pulse duration and shape, a specific transmembrane voltage threshold exists for the manifestation of the electroporation phenomenon. This leads to the definition of an electric field magnitude threshold for electroporation ($E_{th}$). That is, only the cells within areas where $E \geq E_{th}$ are electroporated. If a second threshold ($E_{ir}$) is reached or surpassed, electroporation will compromise the viability of the cells, i.e., irreversible electroporation will occur.

There are a number of existing technologies used to inactivate bacteria, including ultraviolet light, violet-blue light and photodynamic therapy. The use of cold plasma is also under investigation. The electroporation of bacteria is also known. The cell membrane structure of the bacteria and/or its biochemical pathways are disrupted by placing electrodes on a surface or in a liquid and by applying an appropriate voltage, thereby inducing inactivation of the bacteria. When the bacteria experiences a high electrical field pores are induced in the cell membranes of the bacteria and start to close again once the electrical field is discontinued. This process is called reversible electroporation. If the cells are exposed to an even higher electrical field, the induced pores become so large that after discontinuation of the field the pores do not close anymore and the cell dies. This process is called irreversible electroporation and is used to inactivate microorganisms or to kill tumour cells.

Whilst the inactivation of bacteria through electroporation in a laboratory setting is known. However, the use of electroporation for the purposes of directly treating skin to, for example, inactivate or kill the bacteria present on the surface of the skin is not known. Bacteria present on the surface of the skin may be involved in the generation of an unpleasant body odour by transforming components of sweat into malodorous volatiles. Not using electroporation for inactivating bacteria on the skin is primarily due to the difficulty of rendering the bacteria inactive in a safe manner whilst at the same time avoiding unwanted damage or irritation to living skin cells just below the interface between the stratum corneum and the next layer in the epidermis.

Another important issue is the need to ensure that no dangerous electrical currents are induced through the human body. In particular, nerves can be activated by electrical effects which could lead to pain sensation and/or involuntary muscle contraction. Whilst it is known to treat tumours within the human body using electroporation, the applied electroporation pulses have to be synchronized with the patient's heartbeat to prevent heart rhythm problems.

There is also a requirement to ensure that no excess heat is generated when carrying out the electroporation of skin. Sweat contains salt ions typically in the order of 4.5 g/L Sodium Chloride. Although with a relatively dry armpit, a high electrical field strength can be maintained relatively easily and with relatively low electrical current, a wet, sweaty armpit which constitutes a relatively low electrical resistance will inevitably result in a higher electrical current being generated to maintain the required electrical field strength.

A dermal electroporation device is known from WO2013066427A and primarily relates to the use of electroporation for the purpose of delivering drugs to dermal tissue. US2007060862A2 also discloses a transdermal delivery device in which the electrodes are used to control a current flow through the skin.

SUMMARY OF THE INVENTION

It is an object of the invention to provide a device for electroporating bacteria present on a skin surface, i.e. on the stratum corneum layer, such to inactivate these bacteria, without damaging or causing irritation to living skin cells located at the interface with the stratum corneum layer and the epidermis or within the epidermis, thereby overcoming or substantially alleviating the problems referred to above. In particular, the device of the invention can be used to decrease body odour caused by the presence of such bacteria on the skin surface, i.e. on the stratum corneum, such as the bacteria found in the axilla region of the body.

Although bacteria can be present in the glands as well as on the stratum corneum, it is thought that the bacteria on the skin surface is primarily responsible for the majority of malodour, since the secretions of glands are initially odourless. Therefore, it is the bacteria present on the skin surface, i.e. on the stratum corneum, which is the primary target for treatment by the device and method of the present invention.

In the context of the present specification, the "inactivation" of bacteria refers to the death or slowing of the metabolic rate and/or reproduction system of the bacterial cells.

It has been established that to prevent damage to living human cells just below the interface of stratum corneum and the next layer in the epidermis, the electrical field strength needs to drop over the stratum corneum from 30 kV/cm and its surface to about 1-3 kV/cm at the interface of the stratum corneum with the next layer of the epidermis. This understanding is based on the fact that the electroporation effect scales with the diameter of the biological cell and that the bacteria of interest typically have a diameter in the order of one micron, whilst a human cell has a diameter in the order of a factor of ten larger. Consequently, when a one micron sized bacterial cell will be irreversibly electroporated at an electrical field strength of 30 kV/cm, a human cell will be irreversibly electroporated at an electrical field strength of around 3 kV/cm, and reversibly electroporated at an electrical field strength of around 1 to 3 kV/cm.

At present, there is no electroporation device available that provides the required drop in electrical field strength that would make it suitable for use in inactivating bacteria present on the skin surface and, therefore, enable such a device to be used to reduce undesirable body odour caused by such bacteria.

According to the present invention, there is provided a device for the electroporation of bacterial cells present on the surface of the stratum corneum layer of a person's skin, comprising:
electrodes positionable in the vicinity of said surface;
a generator to control and supply a predetermined voltage to the electrodes to generate an electrical field having a strength in the order of 10 to 50 kV/cm at said surface to inactivate bacterial cells present on said surface;
wherein the electrodes are configured so that the strength of the electrical field reduces as a function of the depth of penetration into the stratum corneum layer from said surface to 3 kV/cm or less at a depth of between 5 and 15 micron, preferably between 5 and 10 micron.

By configuring the electrodes such that the electrical field strength reduces to 3 kV/cm or less at a depth of between 5 and 15 micron, preferably between 5 and 10 micron, the electrical field strength will generally only have sufficient strength to inactivate bacteria cells present on the stratum corneum and, at least to some extent, those bacterial cells present within the stratum corneum. However, the electrical field strength will not be high enough to have any appreciable effect on living skin cells in the epidermis below the stratum corneum or at the interface between the stratum corneum and the epidermis.

The electrodes preferably comprise at least one positive and at least one negative electrode, the positive and negative electrodes being in the same plane and being spaced from each other by a predetermined distance to control the strength of the electrical field at a predetermined penetration depth of between 5 and 15 micron, preferably between 5 and 10 micron. By controlling the spacing between the electrodes, the strength of the electrical field at a predetermined depth of penetration can be controlled in order to reduce any effect of the electrical field on living tissue.

In some embodiments, the positive and negative electrodes may be spaced from each other by a distance of 10 micron or less. A separation distance of less than or equal to 10 micron can be considered to be an optimum distance in relation to an average thickness of the stratum corneum, with the aim of ensuring that the electrical field strength at the interface between the stratum corneum and the epidermis is at or below 3 kV/cm. It is also envisaged that the electrodes could be separated by 5 micron to provide an electrical field strength below 3 kV/cm at a penetration depth of 8 micron.

In other embodiments, the device comprises a plurality of positive and negative electrodes, wherein the positive electrodes are positioned in a first plane and the negative electrodes are position in a second plane adjacent to the first plane. By positioning the electrodes in different planes a steeper reduction in the electrical field strength relative to penetration depth can be achieved.

The electrodes in the first plane and the electrodes in the second plane can be in alignment with each other, and the electrodes in each plane may be separated from each other by a distance of 10 microns or less.

In another embodiment, the electrodes in the first plane and the electrodes in the second plane are offset relative to each other so that an electrode in one plane is located between a pair of electrodes in the other plane. This arrangement can provide an even steeper reduction in the electrical field strength with penetration depth.

The electrode elements in different planes may be isolated from each other by an isolating element.

In some embodiments, the device may incorporate a spacer to space the electrodes from the surface of the stratum corneum.

The electrodes may also be provided with sharpened edges in order to further control the shape and spread of the electrical field.

In preferred embodiments, the generator is operable to supply the electrodes with a pulsed voltage of 10 to 1000 pulses, each pulse have a duration of 1 to 100 microseconds or, more preferably, 50 pulses of 50 microseconds each. It will be appreciated that for a small device that is moved across the surface of the skin in the axilla region, a device capable of generating a higher number of pulses will be required if the treatment time is to be kept within a reasonable period and the axilla is to be treated effectively. By administering a particular Voltage over time profile, activation of the nerves can be prevented. More specifically, a sufficiently high frequency of pulses is used which does not activate the nerves but which is not too high that blockage of nerves occurs.

The electrodes may be attached to a supporting substrate in the form of a sphere, cylinder or planar element. If the supporting substrate is a sphere or cylinder, then it may be rotatably mounted to the housing so that it will roll over the surface of the stratum corneum. A rolling element, such as sphere or cylinder, maintains a smooth, low friction contact with the skin surface thereby maximising contact between the electrodes and the surface.

In some embodiments, the electrodes comprise a plurality of electrode arrays. At least one electrode array may extend in a different direction to at least one other electrode array to generate electrical fields of different orientations. This ensures that non-spherical bacterial cells are properly exposed to the electrical field.

The device may also comprise a hydrodynamic probe to supply fluid of low conductivity to the surface of the stratum corneum in the vicinity of the electrodes. The hydrodynamic probe can be used to supply water or other fluid to the skin surface to control conductivity and/or cooling.

According to the present invention, there is also provided a method of manufacturing an electroporation device operable to inactivate bacterial cells present on the surface of the stratum corneum layer of a person's skin without damaging living skin cells at or below the interface of the stratum corneum layer with the epidermis, the device including electrodes positionable in the vicinity of the surface of the stratum corneum, and a generator to supply a voltage to the electrodes to generate an electrical field having a strength in the order of 10 to 50 kV/cm at said surface to inactivate bacterial cells present on said surface, the method including the step of positioning the electrodes relative to each other so that the strength of the electrical field reduces as a function of the depth of penetration into the stratum corneum layer from said surface to 3 kV/cm or less at a depth of between 5 and 15 micron, preferably between 5 and 10 micron, such that during use of the device the electrical field will have sufficient strength to inactivate bacteria cells present on the stratum corneum while at the same time the electrical field is not strong enough to appreciable effect living skin cells in the epidermis below the stratum corneum or at the interface between the stratum corneum and the epidermis.

In a preferred embodiment, the generator is configured to supply a voltage to the electrodes to generate an electrical field having a strength in the order of 25 to 35 kV/cm at said surface.

In preferred embodiments, the voltage driver circuit includes an electrical current limiter to suppress current levels and thereby prevent activation of nerves.

These and other aspects of the invention will be apparent from and elucidated with reference to the embodiments described hereinafter.

BRIEF DESCRIPTION OF THE DRAWINGS

Embodiments of the invention will now be described, by way of example only, with reference to the accompanying drawings, in which.

DETAILED DESCRIPTION OF EMBODIMENTS

According to embodiments of the invention, there is provided an electric field based device used to combat body odour primary aimed at, but not limited to, treating axillae. The device is preferably either portable or attachable to the skin in the form of a patch/textile etc. and is battery powered.

Figure 1:
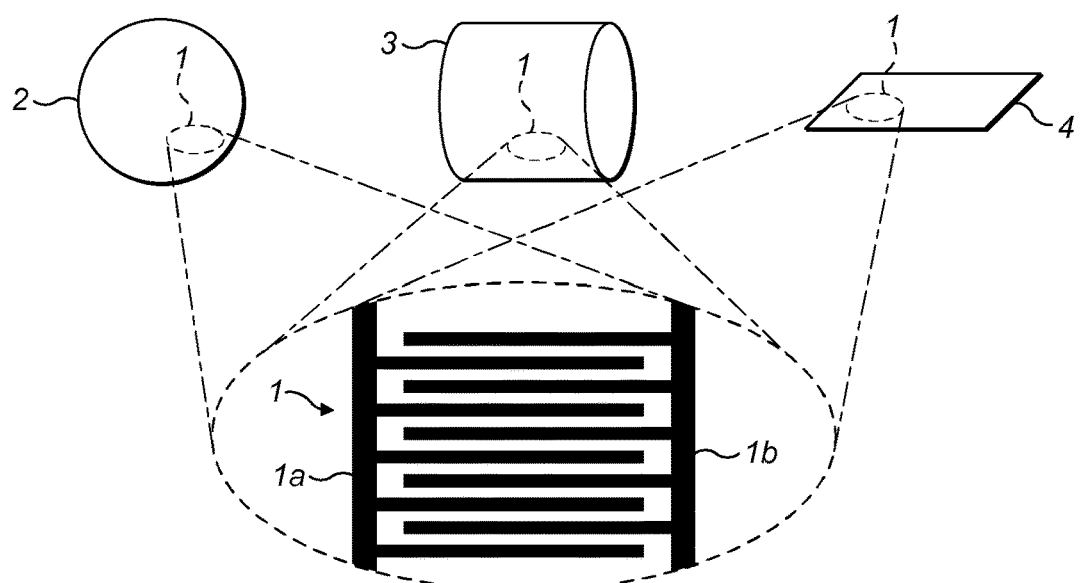
FIG. 1 is a schematic representation of three different surfaces on which an intermittent electrode structure may be provided, together with an enlarged view of such an intermittent electrode structure.

In one embodiment, the device comprises an intermittent electrode array on which a voltage profile over time is enforced to induce an electrical field. FIG. 1 illustrates an enlarged view of a suitable intermittent electrode structure or array 1, having a positive electrode 1a and a negative electrode 1b, which can be attached to the surface of three differently shaped bodies namely, a sphere 2 (see FIG. 1a), a cylinder 3 (see FIG. 1b) and a planar or sheet-like element 4 (see FIG. 1c).

Figure 2:
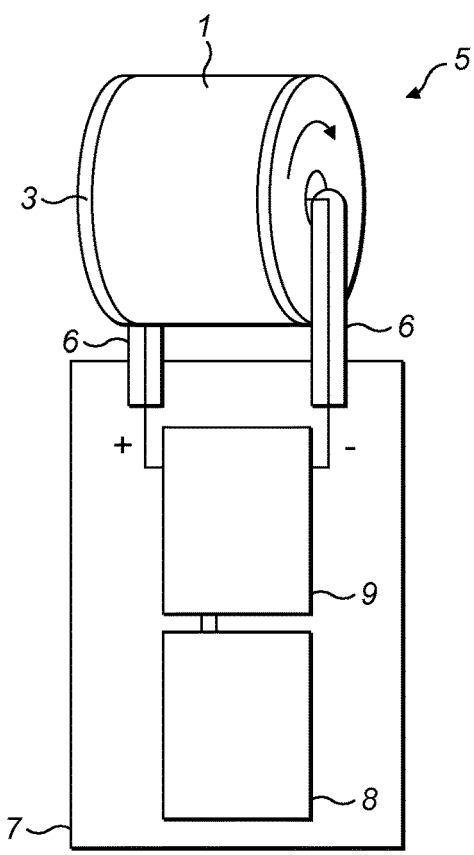
FIG. 2 shows a schematic illustration of a hand-held device incorporating a cylindrical electrode, which is one of the options shown in FIG. 1.

FIG. 2 shows a schematic illustration of a hand-held device 5 incorporating the cylindrical electrode 3, as shown in FIG. 1, and which is mounted for rotation about its longitudinal axis between arms 6, so that it will roll freely across a skin surface during use with minimum friction. Device 5 includes a housing 7 containing a power source, such as a battery 8, and a generator 9 for supplying the electrodes 1 with a predetermined voltage as a function of time so that, when the cylinder 3, to which the intermittent electrode array 1 is attached, is rolled across the skin surface, an electrical field is induced in the skin surface and electroporation is conducted to inactivate bacterial cells. The device 5 may also incorporate an electronic timer (not shown) indicating and limiting the time of use per treatment. The device 5 may also contain circuitry to facilitate recharging of the battery. In preferred embodiments, the electronics and battery 9 are sealed within the housing 6 so that the device 5 can be cleaned easily by a surfactant solution or by holding it under a tap.

It is envisaged that the device 5 will also incorporate a pressure sensitive switch (not shown) so that the electrodes 1a, 1b will automatically activate when the device is pushed against the skin and deactivate when the device 5 is taken out of contact with the skin. Alternatively, it can be provided with a conventional on/off switch.

The device 5 may be provided with a construction that spaces the electrodes 1a, 1b from the skin surface when the device is held against it. Further, if the intermittent electrode array 1 is positioned on a sphere or cylinder 3 that can freely rotate due to the friction with the skin, the skin is stretched and any surface roughness, which can decrease the efficacy of bacteria inactivation, is smoothed out. Whilst it is desirable to inactivate as much of the bacteria as possible, it will also be appreciated that it is unnecessary for all the bacteria present on the skin surface to be inactivated, but that a log reduction of the bacteria in the order of 1 to 3 is sufficient.

It will also be appreciated that other embodiments may comprise features to flatten the skin such as stretchers, lubra strips and lamella etc, either together with one of the structures shown in FIG. 1, or formed in some other shape or configuration. For instance when a lamella structure is moved over the skin under slight pressure the skin will dome between the lamella and will be pushed against the electrodes 1a, 1b located on the surface of the lamella in a smooth manner, thereby minimizing skin surface roughness during contact with the electrodes 1a, 1b. An intermittent electrode array 1 formed on or integrated with a lamella type structure can also increase the degree of contact between the skin and the electrodes 1a, 1b thereby reducing any interference caused by the presence of hair. A more intimate contact may also be achieved by incorporating a vacuum circuit into the device which is operable to apply a mild vacuum, possibly via the lamella structure, or to the skin in the vicinity of the electrodes 1a, 1b, to suck the skin towards the electrodes 1a, 1b. Potentially, the electrode array 1 could also be positioned on the surface of a hair-comb that can be moved through the armpit hair so that its extremities will make contact with the skin.

In some embodiments, the device 5 can incorporate a conductivity detector (not shown). If so, the device 5 can initially be held with the electrodes 1a, 1b positioned against, or close to, the skin and the detector can measure the conductivity at the skin surface. The detector may be coupled to the generator 9 so that it will generate a voltage commensurate with the required electrical field strength required based on the sensed conductivity of the skin. Once this sensing step has been completed, electroporation may then be carried out using the device 5.

In order to successfully electroporate bacterial cells to render them inactive, but at the same time prevent damage or skin irritation, it has been determined that a voltage profile over time of 10 to 1000 pulses each of 1 to 100 microseconds in duration is preferably required or, more preferably, 50 pulses each of 50 microseconds in duration.

As previously indicated, the ideal electrical field strength for inactivating bacteria is in the order of 30 KV/cm, although the generator may be capable of supplying the electrodes with a voltage sufficient to generate an electrical field strength of between 10 kV/cm and 50 kV/cm at the surface of the stratum corneum, although most preferably, the generator is configured to supply the electrodes with a voltage sufficient to generate an electrical field strength of between 25 kV/cm and 35 kV/cm at the surface of the stratum corneum. In order to generate a field strength of between 25 kV/cm and 35 kV/cm at the surface of the stratum corneum using a voltage of 30 kV, the electrodes must be 1 cm apart. However, by using an intermittent electrode array 1 with a distance of for example 200 microns between the electrodes, the required voltage drops down to about 600 Volts, for an electrode separation distance of 30 micron, the required voltage is about 90 Volts and when the electrode separation distance is 10 micron, the required voltage is about 30 Volts.

In order to ensure safety of the device and to prevent the application of an electric current to the body, floating electrodes with respect to the earth are used. As an additional safeguard, the device may also incorporate an electrical current limiter (not shown). Consequently, the above mentioned voltages are manageable and electrical currents through the body will be way below any level that could cause bodily harm.

Figure 3:
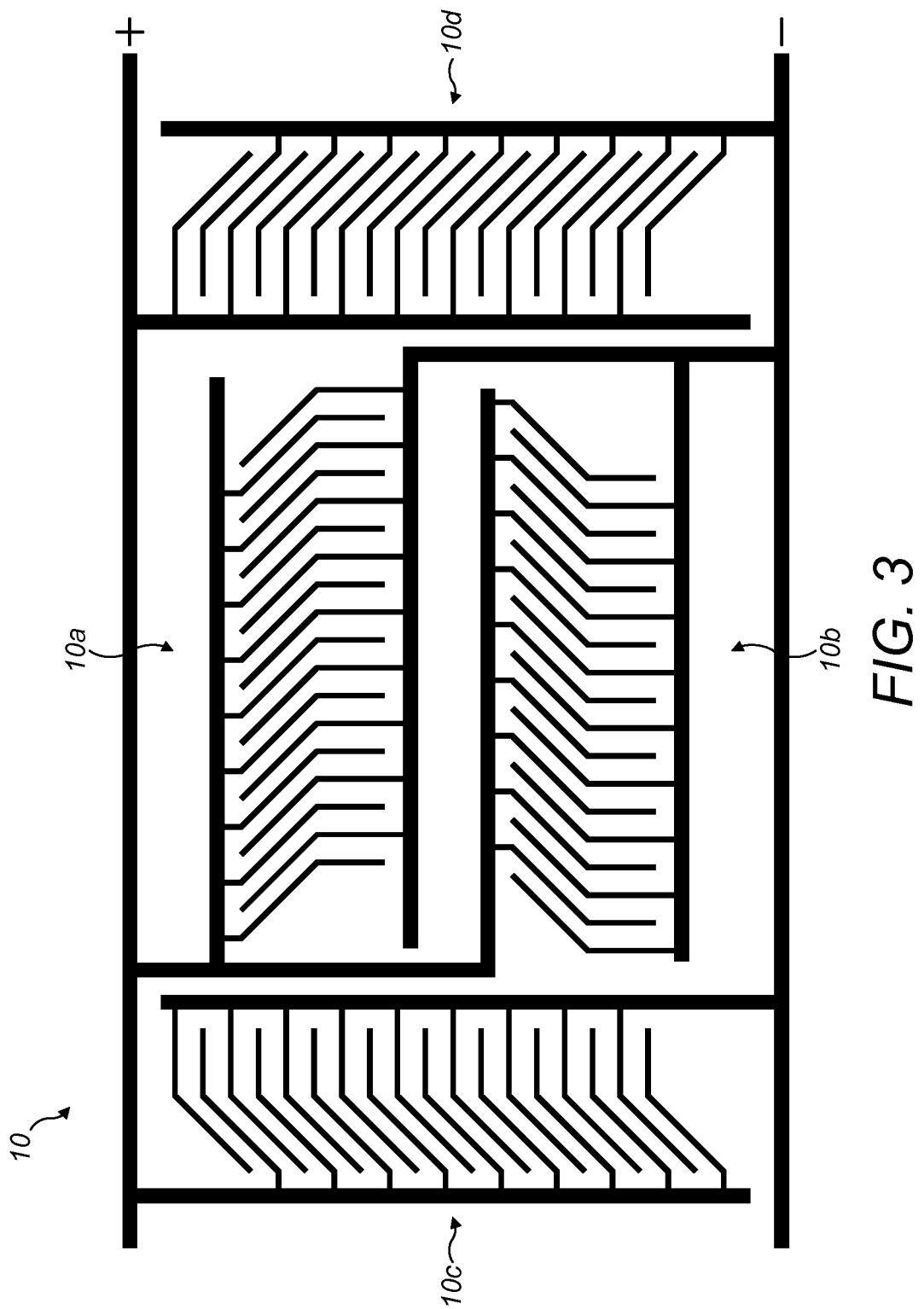
FIG. 3 is a schematic representation of a part of an intermittent electrode array in which electrodes extend in different directions to generate electrical fields in different orientations.

The successful inactivation of bacteria cells largely depends on the orientation of the electrical field, this especially being the case for the inactivation of bacterial cells having a non-spherical shape. A different electrical field orientation can be achieved by providing electrodes extending in different directions so that the bacterial cells are exposed to electrical fields in different orientations as the electrodes are moved across the skin surface. FIG. 3 is a schematic representation of a part of an intermittent electrode array 10 with electrodes positioned in different directions in order to generate electrical fields in different orientations. More specifically, FIG. 3 shows two central arrays 10a, 10b extending in a horizontal direction and two vertical arrays 10c, 10d. A vertical array 10c, 10d extends across the ends of the two central arrays 10a, 10b.

To prevent damage of living human cells just below the interface of the stratum corneum and the next layer in the epidermis, the electrical field strength has to drop over the stratum corneum from 30 kV/cm to about 3 kV/cm, as mentioned above. To achieve this, the electrodes are constructed in a particular way. Possible electrode configurations will now be described in more detail, with reference to FIGS. 4a to 4g and FIG. 5.

Figure 4A:
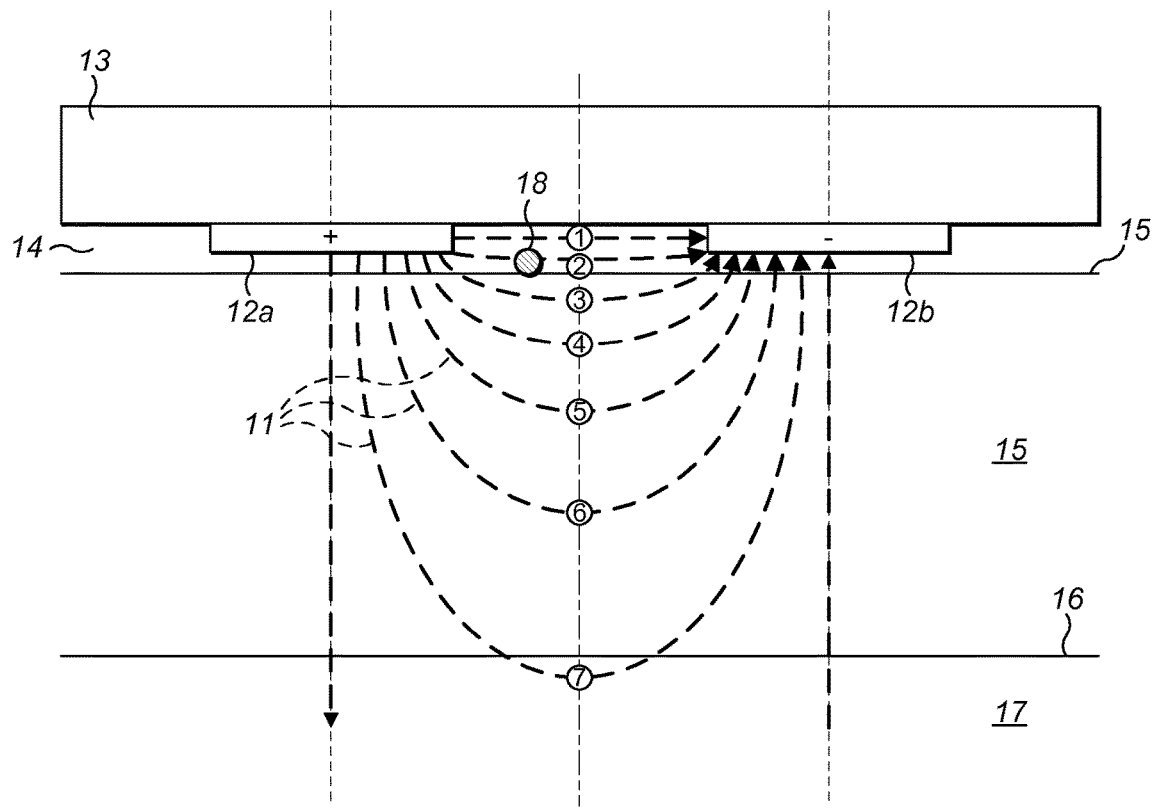
FIG. 4a schematically illustrates a cross-section approximated drawing of the electrical field lines extending between positive and negative electrodes of an intermittent electrode array.

FIG. 4a schematically illustrates a cross-section approximated drawing of the electrical field lines 11 extending between a positive electrode 12a and negative electrode 12b of an intermittent electrode array in which the electrodes 12a, 12b are mounted to a support 13 and are spaced from the skin surface 11, by sweat or air, which forms a gap 14. At the field line indicated by numeral "2" on the surface 15a of the stratum corneum layer 15, a field strength of about 30 kV/cm is required, whilst the field strength at the interface 16 between the stratum corneum layer 15 and the immediately adjacent layer of the epidermis 17 shown by the field line indicated by numeral "7" should be about 3 kV/cm. A bacterial cell 18 is shown on the surface 15 of the stratum corneum 15 and lies within the field strength line indicated by reference numeral "2", so it will become inactivated by the electrical field generated between the electrodes 12a, 12b.

Figure 4B:
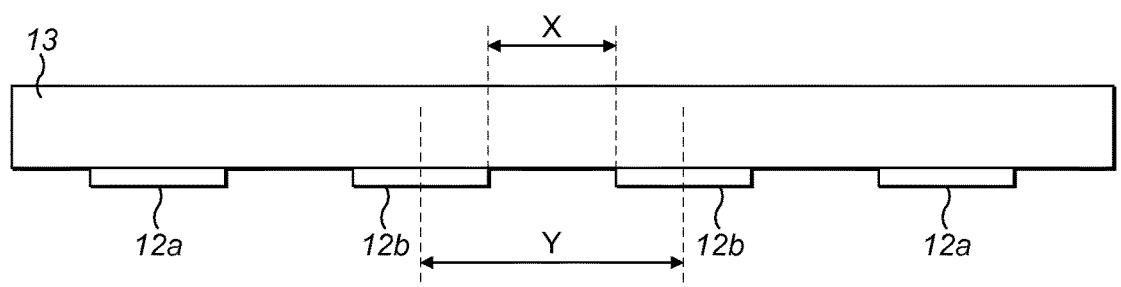
FIG. 4b illustrates the electrode array of FIG. 4a in more detail in order to show the pitch and the gap between adjacent electrodes mounted to a supporting structure.

FIG. 4b illustrates the electrode array in more detail in order to show the pitch and the gap between adjacent electrodes mounted to a supporting structure 13. In FIG. 4b, the gap between adjacent electrodes 12a, 12b is represented by arrow "X", whereas the pitch distance, i.e. the distance between adjacent electrode centres is indicated by arrow "Y".

Figure 4C:
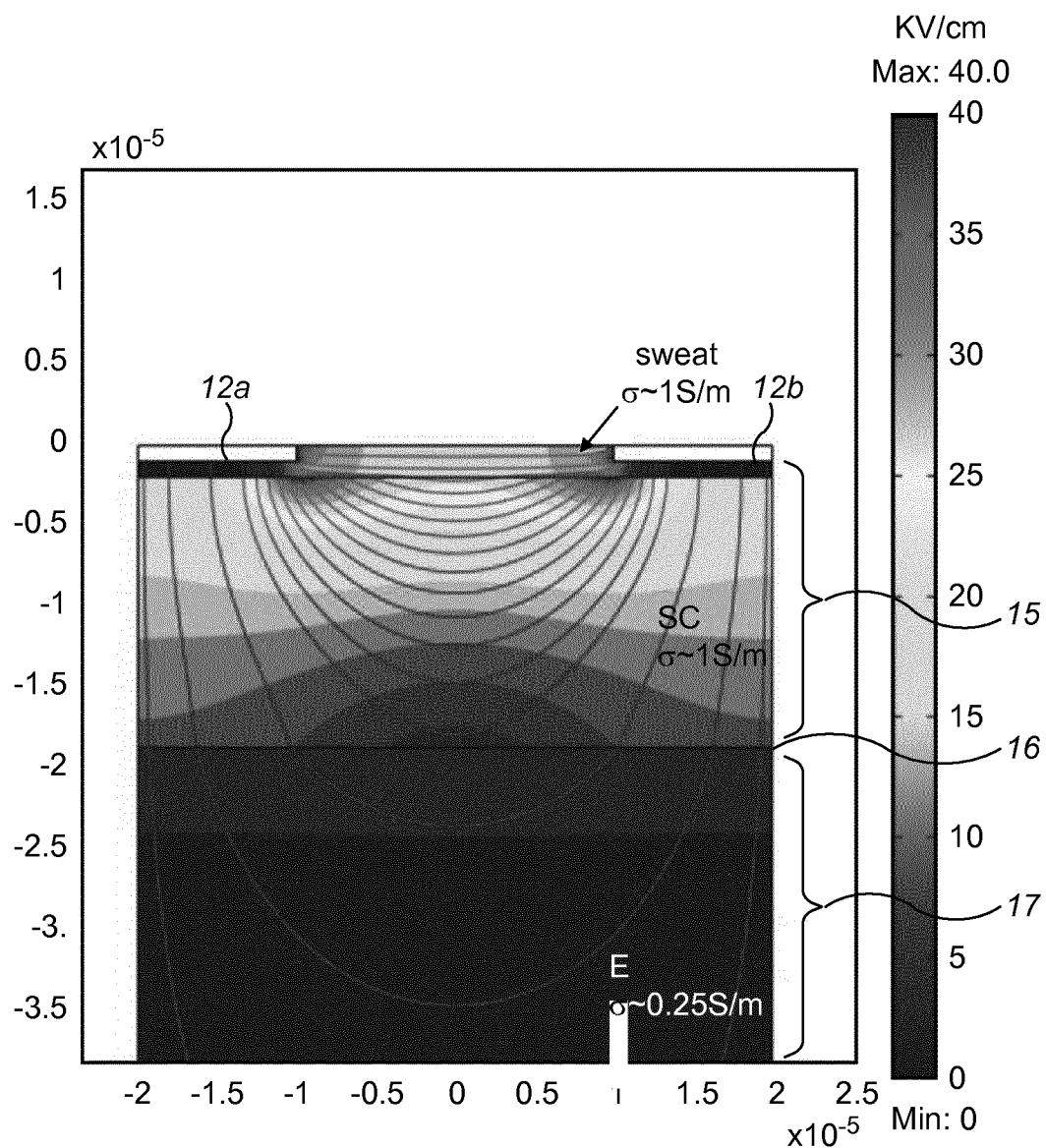
FIG. 4c is a graph to illustrate the electrical field strength generated through the stratum corneum and the epidermis as a result of placing electrodes adjacent to the surface of the stratum corneum and separated therefrom only by a small layer of sweat present on the skin surface, and in which the electrodes are separated by 20 micron.

FIG. 4c is a graph to illustrate the electrical field strength generated through the stratum corneum and the epidermis as a result of placing electrodes adjacent to the surface of the stratum corneum and separated therefrom only by a small layer of sweat present on the skin surface. The electrical field strength on the skin surface is approximately 25 kV/cm, sufficient to inactivate bacteria. However, the graph shows that, with a gap of 20 micron between the electrodes, the electrical field strength at the interface 16 of the stratum corneum 15 and the next layer of the epidermis 17 is well above 3 kV/cm.

Figure 4D:
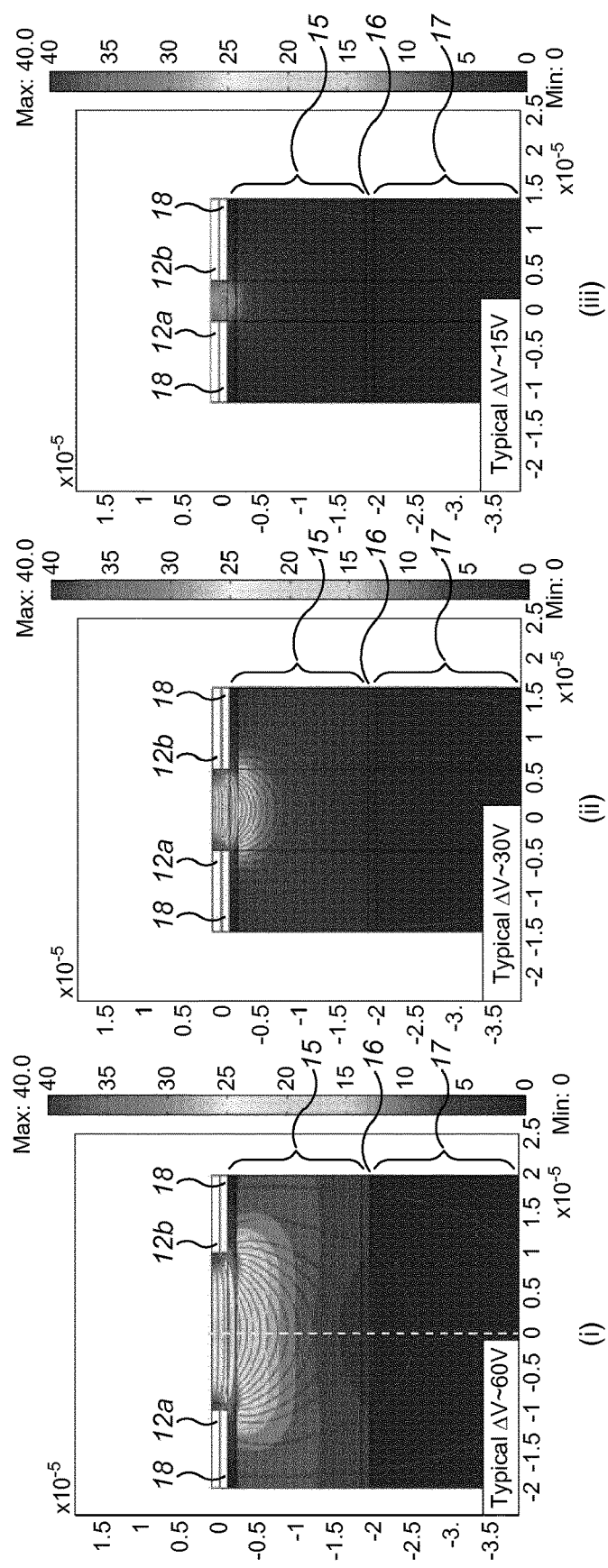
FIGS. 4d(i) to 4d(iii) is a series of three graphs to illustrate how the electrical field strength over the thickness of the stratum corneum decreases, whereas the electrical field strength on the skin between the electrodes increases, as the gap between the electrodes decreases.

FIG. 4d is a series of three graphs to illustrate how the electrical field strength over the thickness of the stratum corneum decreases, whereas the electrical field strength on the skin between the electrodes 12a, 12b increases, as the gap between the electrodes 12a, 12b decreases, and assuming that the voltage is maintained a constant level over the electrodes 12a, 12b. FIG. 4d(i) represents the electrical field strength at a gap distance of 20 micron, FIG. 4d(ii) represents the electrical field strength at a gap distance of 10 micron, and FIG. 4d(iii) represents the electrical field strength at a gap distance of 5 micron.

In certain embodiments, an isolator coating 18 can be positioned on top of the electrodes, i.e. between the electrodes and the surface of the stratum corneum 15. The presence of this isolator can also have an effect on the strength of the electrical field.

Figure 4E:
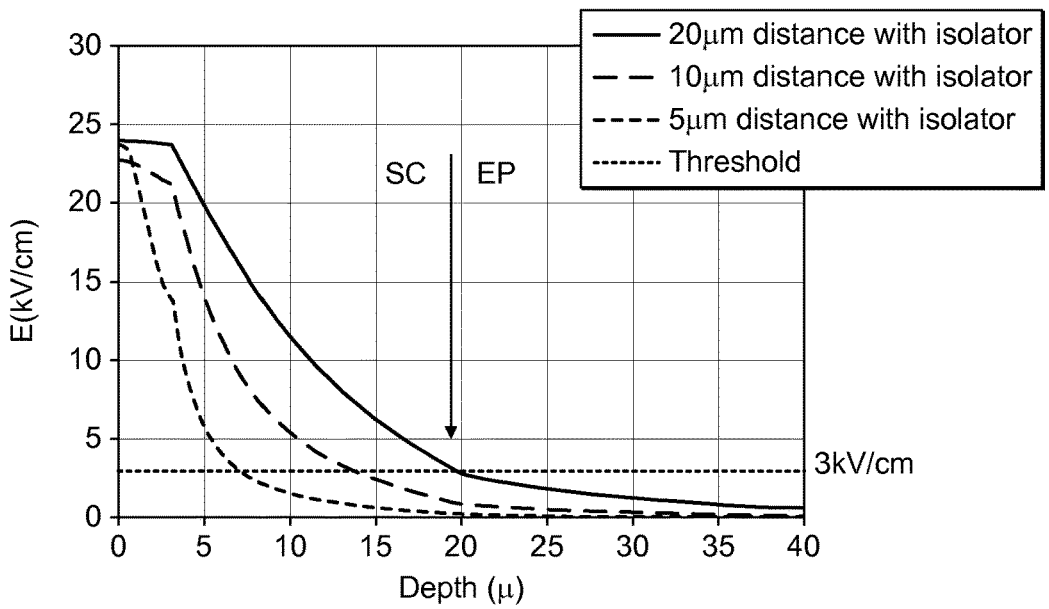
FIG. 4e is a graph to illustrate the electrical field strength as a function of the distance into the skin, with three different electrode separation distances.

In the graph of FIG. 4e, the decrease of field strength over the stratum corneum 15 as function of gap distance between the electrodes 12a,12b is illustrated. It will be noted that, when the gap distance is in the order of 10 micron, the electrical field strength drops under 3 kV/cm at the interface between the stratum corneum 15 and the next layer of the epidermis 17, assuming a stratum corneum 15 thickness of 15 micron.

It will also be apparent that, at a depth of 8 micron, the electrical field strength is only below 3 kV/cm when the gap between the electrodes 12a,12b is 5 microns and so this is relevant for treating an area of the skin that has a thinner stratum corneum 15. Whilst the thickness of the stratum corneum 15 can generally be assumed to be 15 micron, the stratum corneum 15 thickness does vary for the different locations of the skin. For example, the stratum corneum 15 thickness in the palms may be in the order of a few hundreds of microns, while in the axilla it can be in the order of 5 to 15 microns. In view of this, the inventors have devised other electrode structures for the purpose of treating areas of the skin where the stratum corneum 15 is thinner and which provide an even larger drop of in the electrical field strength over the stratum corneum 15.

Figure 4F:
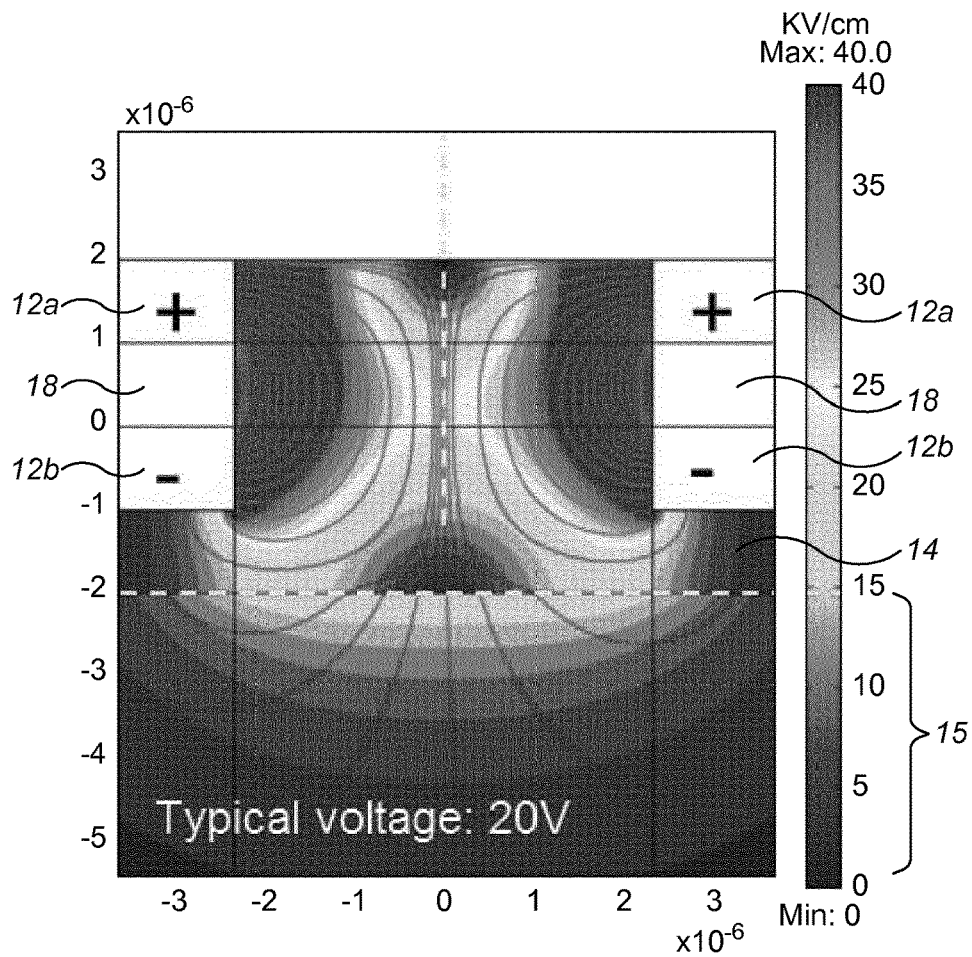
FIG. 4f is a graph to illustrate the electrical field strength generated through the stratum corneum and the epidermis as a result of placing electrodes adjacent to the surface of the stratum corneum, but in which the positive electrodes are located in a different plane to the negative electrodes.

FIG. 4f is a graph to illustrate the electrical field strength generated through the stratum corneum 15 and the epidermis 17 as a result of placing electrodes 12a,12b adjacent to the surface 15a of the stratum corneum 15, but in which the positive electrodes 12a are located in a different plane to the negative electrodes 12b. In the illustrated embodiment, the negative electrodes 12b are positioned closest to the surface 15a of the stratum corneum 15, and separated only therefrom by a thin layer of sweat, whereas the positive electrodes 12a are located directly above the negative electrodes 12b. Each negative electrode 12b is separated from its associated positive electrode 12a by an isolator 14. In the illustrated embodiment, the lateral distance or gap between electrodes 12a,12b, in a direction extending parallel to the plane of the surface 15a, is 5 micron.

Figure 4G:
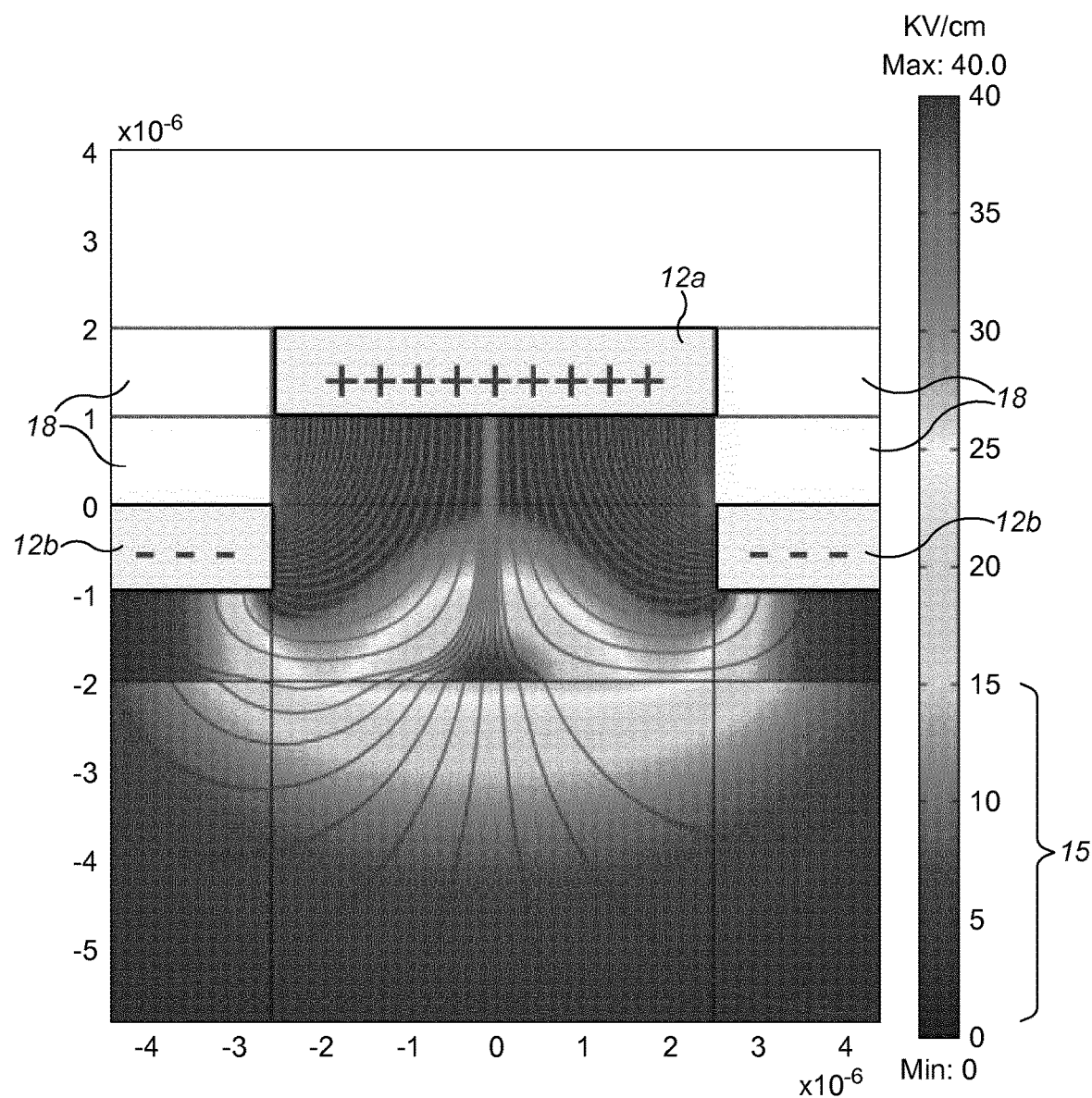
FIG. 4g is a graph which is similar to that shown in FIG. 4f, except that, in addition to being in separate planes, the electrodes are offset or shifted with respect to each other so that the positive electrodes in one plane are positioned between the negative electrodes occupying the adjacent plane.

FIG. 4g shows a graph, which is similar to that shown in FIG. 4f, in which the electrodes 12a,12b are placed in two different planes, except that in FIG. 4g, the electrodes 12a,12b are also offset or shifted with respect to each other so that the positive electrodes 12a in one plane are positioned between negative electrodes 12b occupying the adjacent plane. Reference is also made to the following table which identifies the electrical field strength of the electrode structures described above at three different skin penetration depths from the surface of the stratum corneum 15.

| Pitch in micron | Gap in micron | Isolation coating between electrodes and skin (no coating at the sides of the electrodes) | Structure | E field in kV/cm between the electrodes/% coverage of high enough electrical field of skin surface | E field in kV/cm at interface of SC and next layer of Epidermis (set to 15 micron) | E field in kV/cm at a depth of 5 micron into the SC |
|---|---|---|---|---|---|---|
| 30 | 20 | N | FIG. 4c | 25-35/66% | 9 | 23 |
| 30 | 20 | Y | FIG. 4d | 20-35/66% | 4 | 16 |
| 20 | 10 | Y | FIG. 4d | 20-40/50% | 1.5 | 9 |
| 15 | 5 | Y | FIG. 4d | 15-40/18% | 0.7 | 5 |
| 15 | 5 | N | FIG. 4f | 5-40/18% | 0.2 | 3 |
| 15 | 5 | N | FIG. 4g | 10-40/25% | 0.1 | 2 |

From the above table, it will be appreciated that electrode structures having a smaller gap distance between electrodes 12a,12b show a steep decrease in electrical field strength as a function of the penetration depth into the stratum corneum 15, whereas those embodiments in which the electrodes 12a,12b are placed in two different planes show a steeper decrease in electrical field strength, with the offset electrodes 12a,12b showing the greatest decrease as a function of penetration depth. In should be noted that the electrical field strength between the electrodes 12a,12b is not uniform and so the coverage of the skin surface by a high enough electrical field is estimated in the above table. However, by reducing the electrode width this coverage can be improved. Furthermore, the time required for electroporation is about 5 millisecond while about 10 seconds is available and even with a coverage of 20% by a high enough electrical field, a 100% efficacy can be reached by moving the electrodes 12a,12b over the skin in a period of 25 milliseconds. Assuming an electrode surface area of 1 square centimeter and assuming an armpit surface area of 50 square cm the complete armpit can be treated in 2500 milliseconds (2.5 seconds).

In the previous calculations, the stratum corneum 15 is considered to be wet and so a conductivity of 0.1 S/m can be assumed. However, when the stratum corneum 15 is dry, the conductivity can be assumed to be 0.0001 S/m. The below table shows the effect on electrical field strength of the electrode structures of FIGS. 4d and 4g at three positions namely, between the electrodes 12a,12b, at a penetration depth of 15 micron and at a penetration depth of 5 micron. It will be appreciated from a comparison of the data between the above table and that of the table below that the overall difference between a wet and dry stratum corneum 15 is minor.

| Pitch in micron | Gap in micron | Isolation coating between electrodes and skin (no coating at the sides of the electrodes) | Structure | E field in kV/cm between the electrodes/% coverage of high enough electrical field of skin surface | E field in kV/cm at interface of the Stratum corneum (SC) and next layer of Epidermis (set to 15 micron) | E field in kV/cm at a depth of 5 micron into the Stratum corneum (SC) |
|---|---|---|---|---|---|---|
| 15 | 5 | Y | FIG. 4d | 15-40/18% | 0.75 (wet SC) | 5.00 (wet SC) |
| 15 | 5 | Y | FIG. 4d | 15-40/18% | 0.53 (dry SC) | 6.00 (dry SC) |
| 15 | 5 | N | FIG. 4g | 10-40/25% | 0.13 (wet SC) | 2.26 (wet SC) |
| 15 | 5 | N | FIG. 4g | 10-40/25% | 0.16 (dry SC) | 2.30 (dry SC) |

Figure 5:
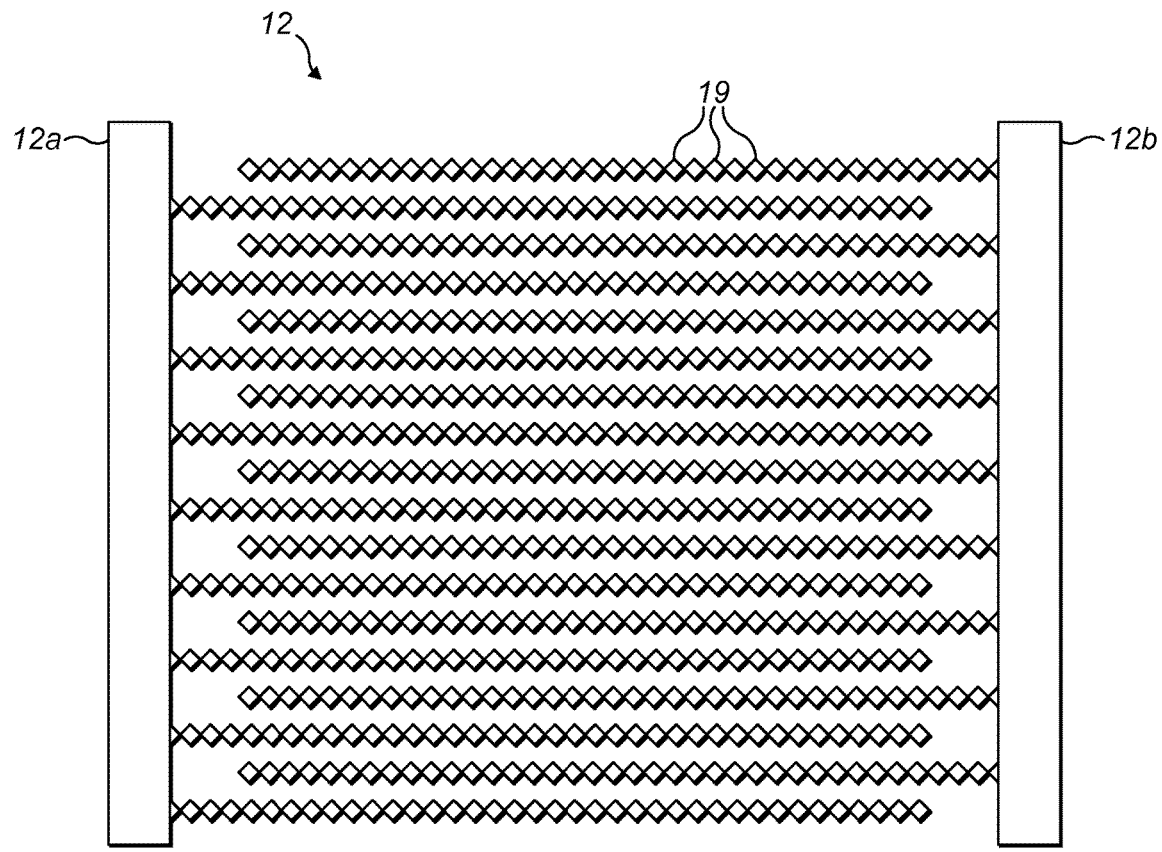
FIG. 5 is a plan view of an electrode structure in which the electrodes are provided with sharp or pointed edges.
Figure 6:
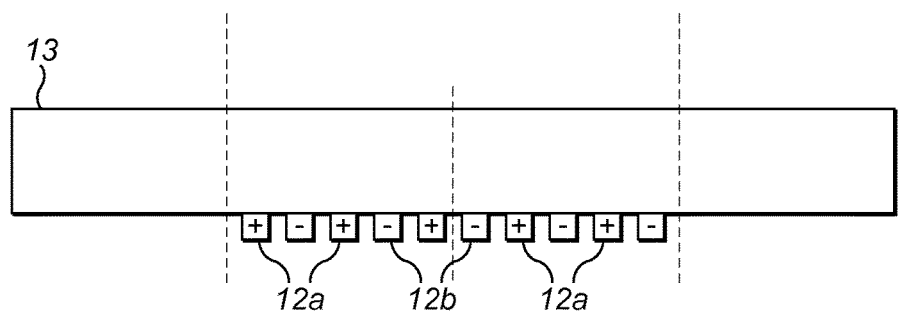
FIG. 6 shows a cross-sectional side elevation of an electrode array in which the electrodes mounted to an electrode support and are shaped as pillars.

In other embodiments consideration can also be given to decreasing the electrical field over the depth of the stratum corneum 15 by using electrodes in the shape of pillars (in fact approaching a dipole) or by creating sharp edges onto the electrodes in the length direction. FIG. 5 shows a plan view of an electrode structure in which the electrodes 12a,12b are provided with sharp or pointed edges 19, whereas FIG. 6 shows a cross-sectional side elevation in which the electrodes 12a,12b are mounted to an electrode support 13 and have a square cross-section.

It will be appreciated that certain bacteria strains have a more or less spherical shape while other strains have more or less a cylindrical or ellipsoid shape. It is known from the Swan equation that the electroporation effect is dependent on the orientation of the field with respect to the biological membrane. Therefore, in the case of none spherical bacteria, rotating the electrical field direction can enhance the efficacy of the electroporation.

In the embodiments of FIGS. 4a-g, the cross section of the electrodes 12a,12b is shown. The electrodes 12a,12b can take the form of long rods having a length axis that protrudes perpendicular to the plane of the drawing. The electrodes 12a,12b can also take the form shown in FIG. 5. By simply moving and rotating the electrodes 12a,12b relative to the skin, the bacteria on the skin experience different electrical field orientations. Alternatively, the electrodes 12a,12b can be moved across the skin but not rotated, in which case an intermittent electrode array having electrodes 12a,12b in different orientations, such as that shown in FIG. 3, can expose the bacteria on the skin to different electrical field orientations.

The dot-like electrodes 12a,12b of FIG. 5 can be electrically controlled individually using driver electronics to create a rotating electrical field without moving or rotating the electrode structures. Furthermore, by applying different voltages on the individual electrodes 12a,12b over time the resulting electrical field can be rotated thereby increasing the efficacy of inactivation for those bacteria with a non spherical aspect ratio. The electrical drivers can be based on active matrix technology as substrate. Such an arrangement is a cheap way to generate array of individually addressable electrodes (to e.g. rotate field); compatible with curved or flexible substrates.

In order to ensure that electroporation can be carried out with both wet and dry armpits without any unacceptable increase in skin temperature, a voltage profile over time can be chosen such that an effective electroporation generates an acceptable temperature increase of the skin. It has been found that for pulses of 50 microseconds up to 100 pulses as function of electrode gap of between 5 and 10 micron, the temperature increase on 5 micron depth into the stratum corneum 15 remains below 45 degrees Celsius.

A further embodiment is envisaged in which the intermittent electrode array is combined with a hydrodynamic probe which will feed demineralised or tap water of low conductivity to the skin, thereby diluting sweat in order to lower the salt concentration of the liquid on the skin. This will reduce any heating effect. Ideally, the probe will be capable of aspirating liquid as well as delivering it to the skin to ensure that no dripping occurs. If the device incorporates a hydrodynamic probe, it will also have a refillable reservoir for storing liquid and a pump or pumps capable of dispensing the liquid onto the skin and aspirating the liquid from the skin.

The hydrodynamic probe may contain additional substances that counteract irritation and will work in a smoothing manner on the skin and may also be able to direct a jet of dry, possibly heated, air in order to dry the armpit before exposing it to an electrical field. The hydrodynamic probe could also be used to dispense particular chemicals, such as a salt solution, with similar ion content as sweat or a solution representing a mild acid such as Citric acid in low concentration. This can have the result of reducing the required electrical field strength by about a factor of two, while maintaining the same bacterial inactivation efficacy. Even dispensing a solution with lowered ph (for instance a citrate solution of 0.05 M with a pH of 4.2) using a probe can substantially increase the inactivation level which could be used to reduce to number of pulses and thereby reduce potential effects on the epidermis which would otherwise be cause by a higher current generation.

Although it is envisaged that the device of the invention will rely primarily on the principle of electroporation in order to inactivate bacterial cells, it is possible to integrate other inactivation technologies that can be used simultaneously or consecutively with electroporation. For example, the device may rely on electroporation in conjunction with light or cold plasma bacterial inactivation techniques.

As indicated previously, the device can incorporate a switch so that when the device is pushed against the skin the electrodes are activated automatically. The hydrodynamic probe can also be operated automatically in this way. In some embodiments the probe may be configured to dispense and simultaneously aspirate fluid for a short period of time prior to automatic activation of the electrodes.

It will be appreciated that the term "comprising" does not exclude other elements or steps and that the indefinite article "a" or "an" does not exclude a plurality. The mere fact that certain measures are recited in mutually different dependent claims does not indicate that a combination of these measures cannot be used to an advantage. Any reference signs in the claims should not be construed as limiting the scope of the claims.

Although claims have been formulated in this application to particular combinations of features, it should be understood that the scope of the disclosure of the present invention also includes any novel features or any novel combinations of features disclosed herein either explicitly or implicitly or any generalisation thereof, whether or not it relates to the same invention as presently claimed in any claim and whether or not it mitigates any or all of the same technical problems as does the parent invention. The applicants hereby give notice that new claims may be formulated to such features and/or combinations of features during the prosecution of the present application or of any further application derived therefrom.

The invention claimed is:

1. A device for the electroporation of bacterial cells present on the surface of the stratum corneum layer of a person's skin, comprising:
    electrodes that comprise at least one positive electrode and at least one negative electrode, wherein the electrodes are positionable in the vicinity of said surface;
    a spacer that comprises an insulator, wherein the insulator is configured to space the electrodes from the surface of the stratum corneum; and
    a generator configured to control and supply a predetermined voltage to the electrodes to generate an electrical field having a strength in the order of 10 to 50 kV/cm at said surface,
    wherein the electrodes further comprise a configuration adapted for reducing the strength of the generated electrical field as a function of the depth of penetration into the stratum corneum layer from 10 to 50 kV/cm at said surface to 3 kV/cm or less at a depth of between 5 and 15 micron or between 5 and 10 micron, and wherein responsive to movement, via the generator or physical movement of the electrodes, of the electrical field generated by the electrodes over the surface, the strength of the electrical field at the surface of 10 to 50 kV/cm is of sufficient strength to inactivate bacteria cells present on the stratum corneum while at the same time the strength of the electrical field below the surface of 3 kV/cm or less will not be strong enough to appreciably effect living skin cells (i) the epidermis below the stratum corneum and (ii) at the interface between the stratum corneum and the epidermis.

2. The device according to claim 1, wherein positive and negative electrodes are in the same plane and spaced from each other by a predetermined distance to control the strength of the electrical field at a predetermined penetration depth of between 5 and 15 micron or between 5 and 10 micron.

3. The device according to claim 2, wherein the positive and negative electrodes are spaced from each other by a distance of 10 micron or less.

4. The device according to claim 3, wherein the electrodes are separated by 5 micron to provide an electrical field strength below 3 kV/cm at a penetration depth of 8 micron.

5. The device according to claim 1, wherein the electrodes further comprise a plurality of positive and negative electrodes, wherein the positive electrodes are positioned in a first plane and the negative electrodes are position in a second plane adjacent to the first plane.

6. The device according to claim 5, wherein the electrodes in the first plane and the electrodes in the second plane are in vertical alignment with each other, the electrodes in the first plane and the electrodes in the second plane being separated from each other by a distance of 10 microns or less, respectively.

7. The device according to claim 5, wherein the electrodes in the first plane and the electrodes in the second plane are laterally offset relative to each other so that an electrode in one plane is laterally located between a pair of electrodes in the other plane.

8. The device according to claim 7, further comprising an isolating element located between electrodes in different planes.

9. The device according to claim 1, wherein the electrodes are further provided with sharpened edges.

10. The device according to claim 1, wherein the generator is operable to supply the electrodes with a pulsed voltage of 10 to 1000 pulses, each pulse have a duration of 1 to 100 microseconds, or operable to supply the electrodes with a pulsed voltage of 50 pulses of 50 microseconds each.

11. The device according to claim 1, wherein the electrodes are attached to a supporting substrate, wherein the supporting substrate is in the form of a sphere, cylinder or planar element.

12. The device according to claim 11, wherein said sphere or cylinder is rotatably mounted to a housing which enables the sphere or cylinder to roll over the surface of the stratum corneum.

13. The device according to claim 1, wherein the electrodes further comprise a plurality of electrode arrays, wherein at least one electrode array extends in a different direction to at least one other electrode array to generate electrical fields of differing orientations.

14. The device according to claim 13, wherein the generator further comprises a voltage driver circuit for generating the supply of a voltage, wherein the voltage driver circuit includes an electrical current limiter to suppress current levels, whereby an activation of nerves in the skin is prevented.

15. The device according to claim 1, wherein the generator is further configured to supply a voltage to the electrodes to generate an electrical field having a strength in the order of 25 to 35 kV/cm on the surface of the stratum corneum.

* * * * *